United States Patent [19]

Vandenbergh

[11] Patent Number: 4,538,459
[45] Date of Patent: Sep. 3, 1985

[54] DRINK CAN MEASURING AND CAN CRUSHING DEVICE

[76] Inventor: John G. Vandenbergh, 3424 Huckabay Cir., Raleigh, N.C. 27612

[21] Appl. No.: 516,656

[22] Filed: Jul. 25, 1983

[51] Int. Cl.³ .............................................. G01L 5/02
[52] U.S. Cl. ..................................... 73/379; 100/902; 100/99; 272/130
[58] Field of Search ................. 73/379, 380, 381, 821; 100/99, 902; 272/67, 130

[56] References Cited

U.S. PATENT DOCUMENTS

| | | | |
|---|---|---|---|
| 1,707,449 | 4/1929 | Rodale | 272/130 |
| 2,680,967 | 6/1954 | Newman | 73/379 |
| 2,784,592 | 3/1957 | Newman | 73/379 |
| 3,369,403 | 2/1968 | Carlin et al. | 73/379 |
| 3,898,983 | 8/1975 | Elam | 128/741 |
| 4,337,780 | 7/1982 | Metrick | 128/774 |
| 4,417,512 | 10/1983 | Engelke | 100/902 |
| 4,425,797 | 1/1984 | Morrison | 73/379 |

Primary Examiner—Stewart J. Levy
Assistant Examiner—Hezron E. Williams
Attorney, Agent, or Firm—Mills & Coats

[57] ABSTRACT

This invention is a strength measuring device utilizing changes in air pressure. The bellows portion of the device is a standard soft drink or beer can. The purposes of the present invention are two-fold; first, to measure the strength of the user thereof and secondly, to crush the can for more compact storage prior to disposal.

9 Claims, 4 Drawing Figures

DRINK CAN MEASURING AND CAN CRUSHING DEVICE

FIELD OF INVENTION

This invention relates to amusement devices and more particularly to means for measuring the strength of the user thereof.

BACKGROUND OF INVENTION

On trips, in bars, and other places where soft drinks, beer and the like are consumed from cans, there is a problem of compacting such cans for disposal. Additionally during consumption of the contents of the cans, there is often boredom due to lack of adequate recreation, particularly during leisure times.

Although complicated and expensive devices for crushing cans have been developed for commercial use, until now individuals have not had any real incentive for disposing of their drink cans in compacted condition. Further, although various types of amusement devices have been developed to entertain people during travel periods, at bars, on picnics, and the like, none of these amusement devices have had the dual purpose of acting as an amusement device as well as providing as a by-product the compacting of drink cans prior to disposal thereof, whether as trash or for recycling.

BRIEF DESCRIPTION OF INVENTION

After much research and study into the above-mentioned problems, the present invention has been developed to provide a means for amusing the user thereof as well as compacting drink cans associated therewith. This is accomplished through the insertion of the male portion of the present invention into the normal opening found in the top of the can and forming an air tight seal therebetween. Then as the can is squeezed in a crushing fashion, the strength of the user will be indicated on a read-out device. Thus the crushing of cans becomes an interesting pastime as well as a competitive game when two or more parties vie for the highest pressure read-out.

In view of the above, it is an object of the present invention to provide a combination muscular strength measuring and can crushing means.

Another object of the present invention is to provide an advertising means which can additionally serve as a recreational means and an incentive means for reducing empty cans to a compact state.

Another object of the present invention is to provide a means for testing the strength of the user thereof while at the same time reducing an empty container to compact state.

Another object of the present invention is to provide a recreational means which is fun to use, creates a competitive atmosphere, and reduces normally bulky trash to a compact state for disposal or recycling.

Another object of the present invention is to provide a pneumatic pressure gauge for insertion to the normal opening of a can to measure the strength of the user thereof as the can is crushed.

Other objects and advantages of the present invention will become apparent and obvious from a study of the following description and the accompanying drawings which are merely illustrative of such invention.

DETAILED DESCRIPTION OF INVENTION

Figure 4:
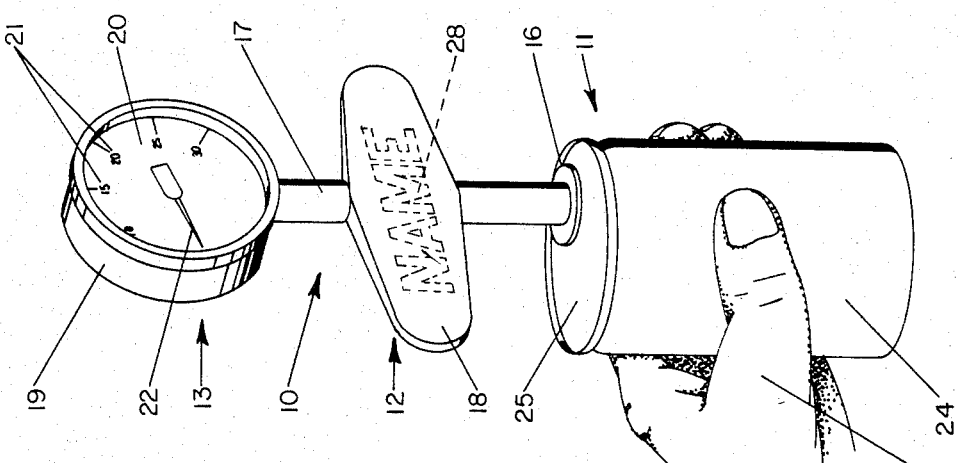
FIG. 4 is a perspective view showing the device of the present invention in use.

With further reference to the drawings, the device of the present invention, indicated generally at 10, includes a can engaging portion 11, a manipulating handle portion 12 and a pressure indicating portion 13.

The bellows/can engaging portion 11 is in the form of a threaded, tapered male plug 14 having a relatively soft, compressible, washer-like seal immediately adjacent thereto. The threads of the male portion are preferably sharp, relatively deep threads for cutting into the can opening and firmly holding the same therein. The washer-like seal is formed from an alcohol and beverage resistance rubber, neoprene, silicone, or the like.

Juxtaposed to seal 15 is a seal backing or flange 16 which is fixedly secured to shaft 17.

Outwardly disposed from the central portion of shaft 17 are wing-like manipulating handles 18.

At the end of shaft 17 opposite plug 14 is an air pressure gauge 19 having a read-out or dial 20 with calibrated indicia 21 thereon. An indicator 22 is operatively mounted adjacent dial 20 to indicate air pressure caused by squeezing of the bellows/can as will hereinafter be described in greater detail.

Although a dial type pressure gauge is shown in the drawings, a linear gauge similar to tire pressure gauges, electronic LED read-out gauges, or the like can obviously be substituted therefor.

The present invention may, of course, be manufactured from a number of different types of metals, from molded plastic, or a combination thereof.

Figure 3:
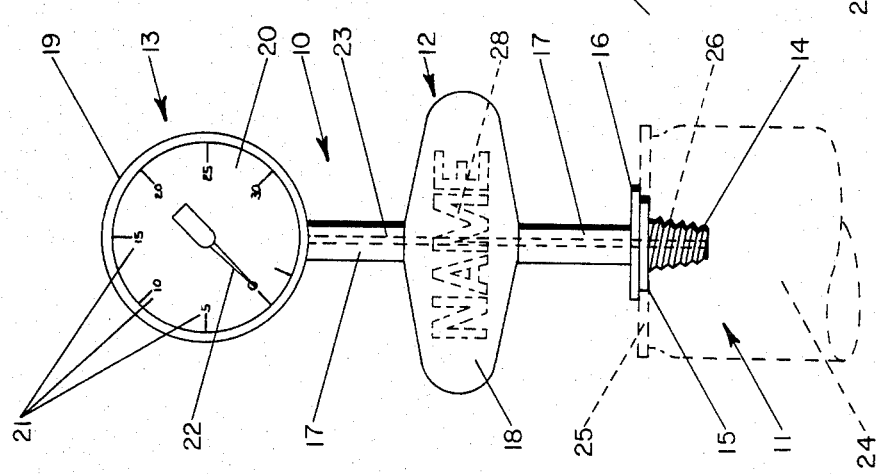
FIG. 3 is a front elevational view thereof showing insertion of the measuring device into the disposable bellows/can.
Figure 2:
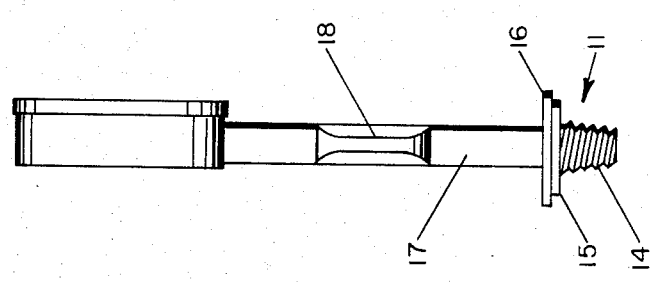
FIG. 2 is a side elevational view thereof.
Figure 1:
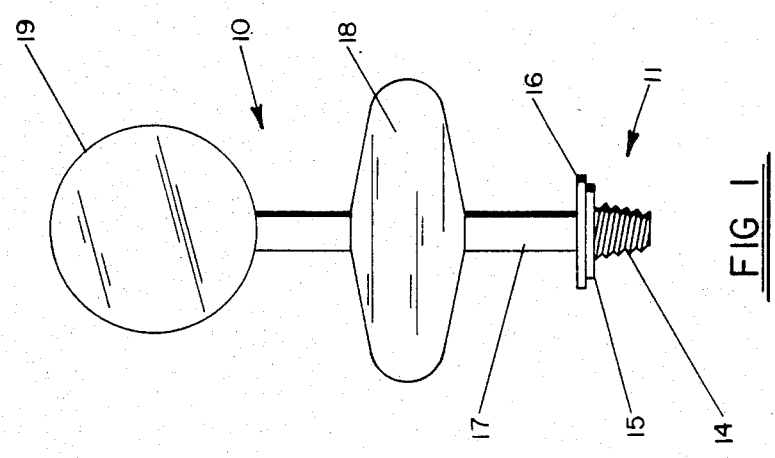
FIG. 1 is a rear elevational view of the strength measuring and can crushing device of the present invention.

An internal passage 23 communicates between the open end of threaded plug 14 through shaft 17 to pressure gauge 19 as can clearly be seen in FIG. 3. This air passage, of course, allows pressure built up adjacent plug 14 to operate the pressure gauge 19.

To use the strength measuring and can crushing device of the present invention, a standard pop-top soft drink or beer can 24 is open and the contents thereof consumed. Next, the deep cutting threads of tapered plug 14 are placed in the normal opening of the can top 25 and handles 18 are used to screw the plug into the can opening 26 until seal 15 is firmly seated against the top to form an air tight connection between the can and the measuring device. Next, the can 24 is grasped in the hand 27 of the user thereof and crushing pressure is applied to such can. The harder the can is squeezed the more it will collapse thus building up internal pressure which is transmitted through air passage 23 with read-out being given by indicator 22 as to the PSI achieved.

Once the bellows/can 24 has been crushed and the strength of the user thereof measured, handles 18 once again are manipulated to remove the device 10 of the present invention from such can. The can may then be disposed of in a collapsed condition thus taking up less space in whatever repository is used to hold empty cans prior to disposal either as trash or through recycling.

From the above it can be seen that the present invention has the advantage of giving the user thereof an incentive to crush his drink cans while at the same time building up strength in his hands and forearms. The present invention is fun to use, is simple to install and remove, and can be used as an advertising medium with a name or logo being placed thereon as indicated at 28.

The present invention can, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. The method of measuring muscular strength while reducing the size of can type containers prior to disposal thereof comprising: opening said can; emptying at least a portion of the contents of said can; sealingly placing a portion of an air pressure measuring means having a pressure indicator in said opening; squeezing said can to at least partially collapse the same so as to cause air inside said can to communicate into said air pressure measuring means; and removing said measuring means from said can whereby the same will be in a compact condition when disposed of.

2. The method of claim 1 wherein said can is of the soft drink type.

3. The method of claim 2 wherein said can includes a pop top type opening.

4. The method of claim 1 wherein said can is of the beer can type.

5. The method of claim 4 wherein said can includes a pop top type opening.

6. The method of claim 1 wherein the measuring means measures the muscular strength of the squeezer of said can.

7. The method of claim 6 wherein the measuring means is an air gauge.

8. The method of claim 7 wherein said air gauge measures pounds per square inch.

9. The method of measuring muscular strength of an individual while he crushes a beverage can comprising: opening said can; emptying at least a portion of the beverage contents of said can; sealingly placing a portion of an air pressure measuring means having a strength indicator in said opening; squeezing said can to at least partially collapse the same as to cause air inside said can to communicate into said air pressure measuring means; and reading said strength indicator portion of said measuring means.

* * * * *